(12) United States Patent
Pak et al.

(10) Patent No.: US 10,758,272 B1
(45) Date of Patent: Sep. 1, 2020

(54) SURGICAL TOOL FOR HAIR TRANSPLANT

(71) Applicants: Jae Pak, Los Angeles, CA (US); William Rassman, Los Angeles, CA (US)

(72) Inventors: Jae Pak, Los Angeles, CA (US); William Rassman, Los Angeles, CA (US)

(*) Notice: Subject to any disclaimer, the term of this patent is extended or adjusted under 35 U.S.C. 154(b) by 0 days.

(21) Appl. No.: 16/548,056

(22) Filed: Aug. 22, 2019

(51) Int. Cl.
*A61B 17/34* (2006.01)
*A61B 17/00* (2006.01)

(52) U.S. Cl.
CPC ............... *A61B 17/3468* (2013.01); *A61B 2017/00752* (2013.01); *A61B 2017/00969* (2013.01)

(58) Field of Classification Search
None
See application file for complete search history.

(56) References Cited

U.S. PATENT DOCUMENTS

2005/0187573 A1* 8/2005 Rassman ............ A61B 17/3468
606/187
2005/0245952 A1* 11/2005 Feller ............... A61B 17/32053
606/170

* cited by examiner

*Primary Examiner* — Shaun L David
(74) *Attorney, Agent, or Firm* — Venable LLP

(57) ABSTRACT

A surgical instrument and method for implantation of follicular units into the scalp of a patient, including a generally cylindrical handle; a cannula disposed at one end of the cylindrical handle, the cannula having an open port constructed to load and to hold a follicular unit, and the cannula further having a tip end constructed for insertion into an implantation incision at an implantation site; a flap for at least partially closing the open port; a movable lever hinged at one end thereof relative to the cylindrical handle and connected at another end thereof to the flap; and a plunger extending through the cannula and constructed to displace a loaded follicular unit out from the cannula into the implantation incision.

19 Claims, 12 Drawing Sheets

SURGICAL TOOL FOR HAIR TRANSPLANT

BACKGROUND

1. Technical Field

The field generally relates to tools for implanting a follicular unit and methods of use thereof.

2. Discussion of Related Art

Follicular unit excision (FUE) is a process by which individual follicular units are harvested for implantation at an incision site on the scalp. Current practice for handling harvested follicular units includes forceps to hold and implant harvested follicular units or tubular implanters that hold and then implant the harvested follicular units into the scalp. Some tubular implanters implant these follicular units through an intact skin with a sharp tubular implanter while others perform the same function using a dull tubular implanter designed to place these follicular units into premade incisions in the scalp. Practitioners recognize that handling fragile harvested follicular units and transplanting them using forceps could jeopardize the growth of the follicular units by applying unnecessary mechanical stress upon them. One of the most commonly used practices of hair transplantation involves the creation of incision sites followed by the transplantation of a harvested follicular unit into the incision sites either immediately or delayed to be implanted all at the same time. Similarly, sharp implanters can place these follicular units through an intact skin. This process is then repeated until the desired or required amount of harvested follicular units have been implanted into a target area. Such a process is often labor intensive and time consuming because the loading of the implanters add additional time and labor to the process. Thus, there remains a need for a device and method that simultaneously reduces damage to the harvested follicular unit and allows for the rapid loading and implanting of the harvested follicular units without the need to additional time and labor added to the process.

SUMMARY

An embodiment of the instant disclosure herein relates to a surgical instrument for implantation of a follicular unit, having: a generally cylindrical handle; a cannula disposed at one end of the cylindrical handle, the cannula having an open port constructed to load and to hold a follicular unit, and the cannula further having a tip end constructed for insertion into an implantation incision at an implantation site; a flap for at least partially closing the open port; a movable lever hinged at one end thereof relative to the cylindrical handle and connected at another end thereof to the flap, the movable lever being movable between a first position where the flap closes the open port and a second position where the flap is away from the open port and the port remains open; and a plunger extending through the cannula and constructed to displace a loaded follicular unit out from the cannula into the implantation incision in a case where the movable lever is in the first position.

An embodiment of the instant disclosure herein relates to a method for surgical implantation of a follicular unit into an implantation incision at an implantation site, including the steps of: loading a follicular unit into the open port of the surgical instrument by the person implanting the follicular unit described above while the movable lever is in the second position where the flap is away from the open port; moving the movable lever to the first position where the flap at least partially closes the open port; inserting the tip end of the cannula into the implantation incision down to an implantation depth; and operating the plunger while the tip end of the cannula is inserted into the implantation incision and the movable lever is in the first position where the flap closes the open port, so as to displace the loaded follicular unit into the implantation site, while simultaneously withdrawing the tip end of the cannula from the implantation site. In such an embodiment, achieving the best depth for insertion or implantation of the follicular unit appears to be to occlude the orifice of the incision with the instrument so that the instrument itself does not have to enter the wound, but the plunger can drive the follicular unit into the wound, as a nail will be driven into a piece of wood with a hammer. Metaphorically, the wood can have a predrilled hole or the nail can be positioned such that the hammer, once establishing a required depth, can be driven into the wood without a premade hole using a sharp implanter.

BRIEF DESCRIPTION OF THE DRAWINGS

Further objectives and advantages will become apparent from a consideration of the description, drawings, and examples.

DETAILED DESCRIPTION

Figure 1A:
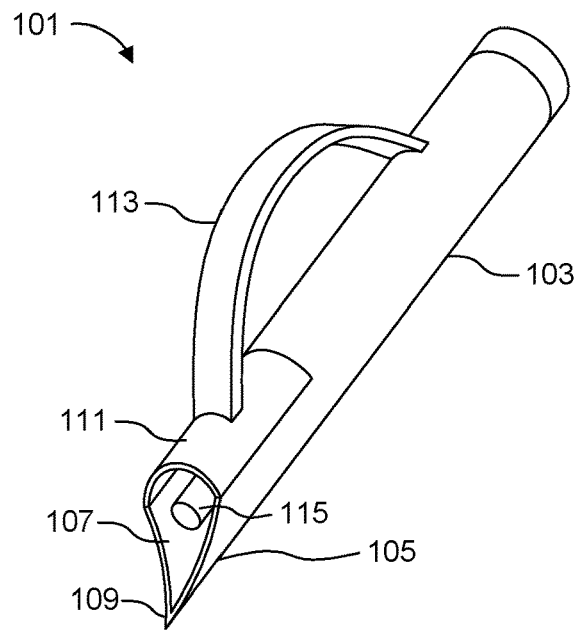
FIGS. 1A and 1B are illustrations depicting a surgical instrument for implantation of a follicular unit according to an embodiment of the disclosure.

Some embodiments of the current disclosure herein are discussed in detail below. In describing embodiments, specific terminology is employed for the sake of clarity. However, the disclosure herein is not intended to be limited to the specific terminology so selected. A person skilled in the relevant art will recognize that other equivalent components can be employed and other methods developed without departing from the broad concepts of the current disclosure herein. All references cited anywhere in this specification, including the Background and Detailed Description sections, are incorporated by reference as if each had been individually incorporated.

The terms "graft" and "follicular unit" are used interchangeably throughout. In general, the terms "graft" and "follicular unit" refer to any piece of hair-bearing tissue that can be transplanted. A harvested graft or follicular unit is a piece of hair-bearing tissue that has been removed from one area and is to be implanted or otherwise transplanted into a separate area. Methods of harvesting grafts or follicular units are known in the art.

The terms "subject" and "patient" are used interchangeably throughout. In general, the terms "subject" and "patient" refer to an individual in need of or in want of a hair transplantation procedure.

The term "target tissue" as used throughout refers to a tissue location to be targeted for a hair transplantation procedure. In some cases, the target tissue is a region on the scalp of a patient or subject. However, the target tissue is not limited to the scalp of a patient or subject and can include other areas of the patient's or subject's epidermis and underlying dermis. The terms "incision site" and "implantation incision" and "premade incision" are used interchangeably throughout and refer to a site on the target tissue which has been or will be surgically manipulated to receive a graft.

The term "cannula" as used throughout refers to a structure having a lumen and configured to accommodate a harvested follicular unit. In some embodiments, the cannula has an overall cylindrical shape, however other structures having a lumen can readily be envisioned. The cannula forms an open port such that the cannula can adopt an open conformation when the open port is unobstructed, and a closed conformation when the open port is covered or sealed. The port thus provides access to a coverable compartment into which a follicular unit may be loaded in preparation for transplant into a transplant site. The cannula may be sharp or dull. More specifically, in some embodiments the cannula has a beveled edge which can be used to penetrate tissue, or make an incision site.

The term "flap" as used throughout refer to a structure configured to reversibly form a cover or seal over an open port of a cannula of a surgical instrument. In some embodiments the flap has a shape that complements the shape of the cannula and/or open port of the cannula. In some embodiments the flap has a distinct shape or design from the cannula and/or open port of the cannula.

The term "plunger" as used throughout refers to a mechanically operable structure which is used at least in part to vacate a harvested hair follicle from the cannula of a surgical instrument.

In general, embodiments of the disclosure herein are related to a follicular unit implanter having either a non-incising tip or an incising tip. The implanter is designed to reduce the manipulation of hair follicles during the implantation process into premade incision sites or through the skin with a percutaneous approach. The implanter has a cannula designed to have an open conformation for facilitated loading of a harvested hair follicle into the lumen of the cannula, and to also have a closed conformation to protect the hair follicle during transport and insertion into the incision site. Device An embodiment of the instant disclosure herein relates to a surgical instrument for implantation of a follicular unit, having: a generally cylindrical handle; a cannula disposed at one end of the cylindrical handle, the cannula having an open port constructed to load and to hold a follicular unit, and the cannula further having a tip end constructed for insertion into an implantation incision at an implantation site; a flap for at least partially closing the open port; a movable lever hinged at one end thereof relative to the cylindrical handle and connected at another end thereof to the flap, the movable lever being movable between a first position where the flap closes the open port and a second position where the flap is away from the open port and the port remains open; and a plunger extending through the cannula and constructed to displace a loaded follicular unit out from the cannula into the implantation incision in a case where the movable lever is in the first position.

An embodiment of the instant disclosure herein relates to the surgical instrument for implantation of a follicular unit above, where the tip end of the cannula has sharp edge configured to penetrate a tissue at the implantation site. In an embodiment, the sharp edge is a beveled edge.

An embodiment of the instant disclosure herein relates to the surgical instrument for implantation of a follicular unit above, where the open port extends longitudinally along the cannula.

An embodiment of the instant disclosure herein relates to the surgical instrument for implantation of a follicular unit above, where the open port extends longitudinally along the cannula and is open completely to the tip end of the cannula.

An embodiment of the instant disclosure herein relates to the surgical instrument for implantation of a follicular unit above, where the open port extends longitudinally along the cannula and is not open completely to the tip end of the cannula.

An embodiment of the instant disclosure herein relates to the surgical instrument for implantation of a follicular unit above, where the open port extends longitudinally along the cannula and radially across about half of the cannula.

An embodiment of the instant disclosure herein relates to the surgical instrument for implantation of a follicular unit above, where the open port extends longitudinally along the cannula and radially across about one third of the cannula.

An embodiment of the instant disclosure herein relates to the surgical instrument for implantation of a follicular unit above, where the tip end of the cannula includes a non-incising pointed tip.

An embodiment of the instant disclosure herein relates to the surgical instrument for implantation of a follicular unit above, where a tip end of the flap includes a non-incising pointed tip.

An embodiment of the instant disclosure herein relates to the surgical instrument for implantation of a follicular unit above, where the movable lever is biased in a direction towards the first position where the flap closes the open port, and movement of the movable lever against the bias causes movement of the movable lever towards the second position where the flap is away from the open port.

An embodiment of the instant disclosure herein relates to the surgical instrument for implantation of a follicular unit above, where the movable lever is biased in a direction towards the second position where the flap is away from the open port, and movement of the movable lever against the bias causes movement of the movable lever in toward the first position where the flap closes the open port.

An embodiment of the instant disclosure herein relates to the surgical instrument for implantation of a follicular unit above, where multiple flaps are actuated by the movable lever and cooperate for at least partial closing of the open port.

An embodiment of the instant disclosure herein relates to the surgical instrument for implantation of a follicular unit above, where the flap completely closes the open port.

Figure 1B:
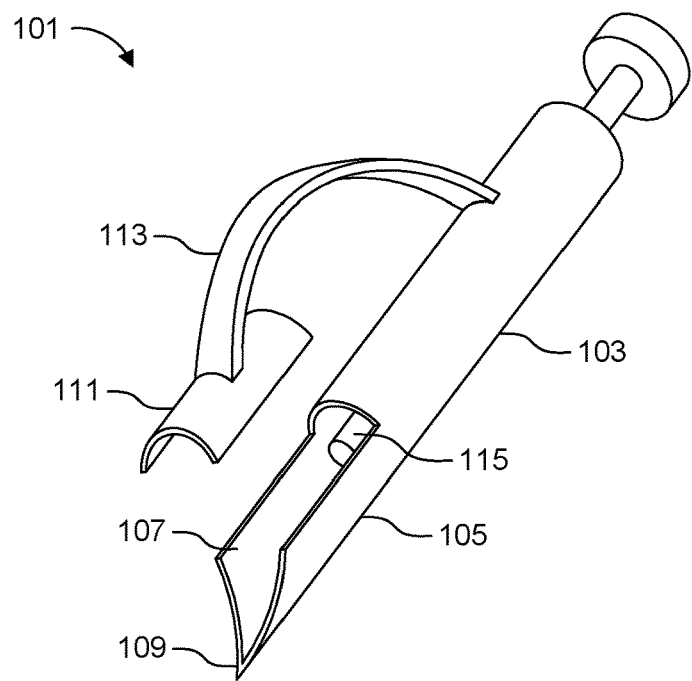

FIGS. 1A-1B are illustrations of a surgical instrument 101 for implantation of a follicular unit according to an embodiment of the disclosure. The surgical instrument of FIGS. 1A and 1B includes: a generally cylindrical handle 103; a cannula 105 disposed at one end of the cylindrical handle 103, the cannula 105 having an open port 107 constructed to load and to hold a follicular unit, and the cannula 105 further having a tip 109 end constructed for insertion into an implantation incision at an implantation site; a flap 111 for at least partially closing the open port 107; a movable lever 113 hinged at one end thereof relative to the cylindrical handle and connected at another end thereof to the flap, the movable lever 113 being movable between a first position where the flap 111 closes the open port (as shown in FIG. 1A) and a second position where the flap 111 is away from the open port and the port remains open (as shown in FIG. 1B); and a plunger 115 extending through the cannula 105 and constructed to displace a loaded follicular unit out from the cannula into the implantation incision in a case where the movable lever is in the first position. In the embodiment depicted, the tip 109 has a beveled edge sharp enough to penetrate tissue at an implantation site and create an incision site for the implantation of the follicular unit. However, in other embodiments the tip is non-incising. In alternative embodiments, the flap 111 has a beveled edge sharp enough to penetrate tissue at an implantation site and create an incision site for the implantation of the follicular unit.

Figure 2A:
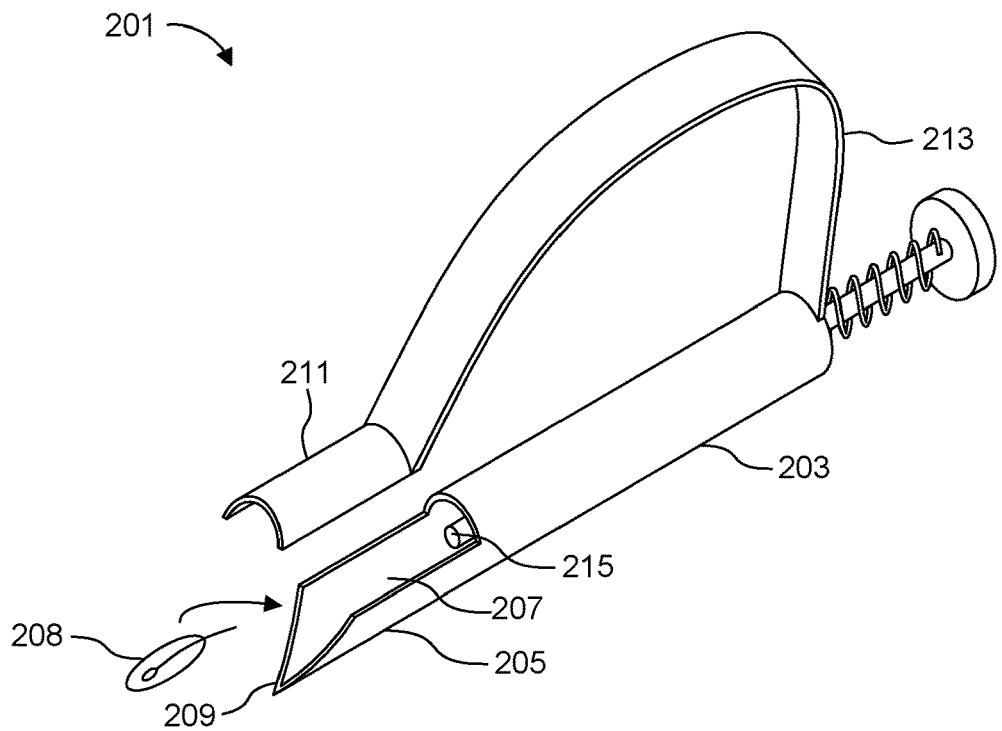
FIGS. 2A-2C are illustrations depicting a surgical instrument for implantation of a follicular unit according to an embodiment of the disclosure.
Figure 2B:
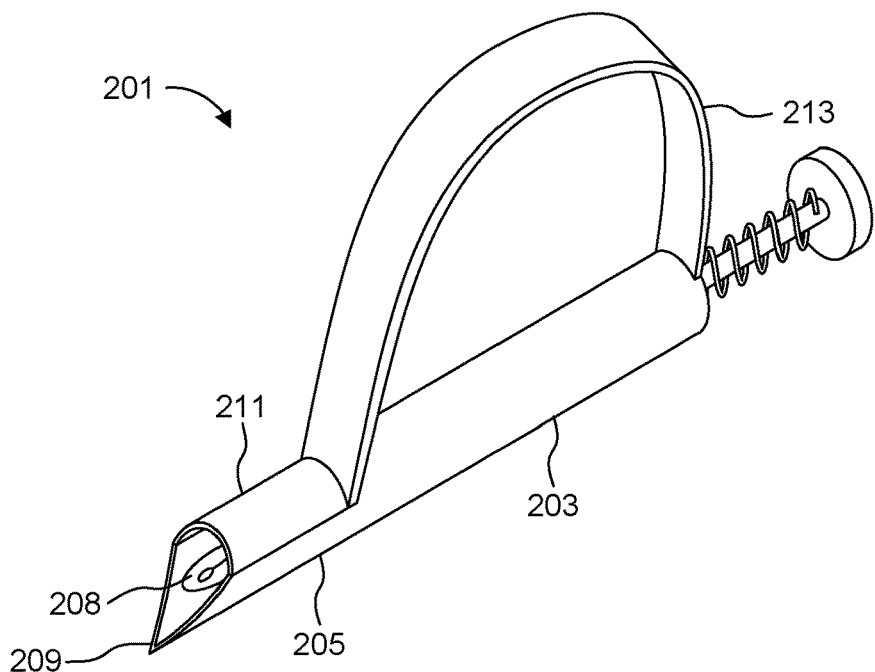
Figure 2C:
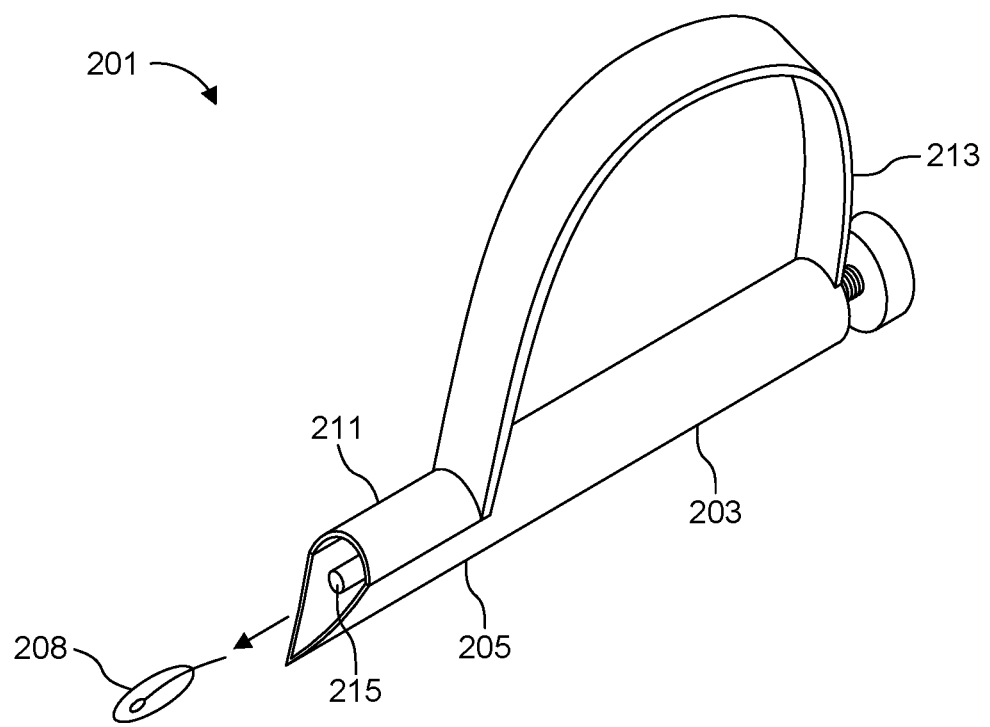

FIGS. 2A-2C are illustrations of a surgical instrument 201 for implantation of a follicular unit according to an embodiment of the disclosure. The surgical instrument of FIGS. 2A-2C includes: a generally cylindrical handle 203; a cannula 205 disposed at one end of the cylindrical handle 203, the cannula 205 having an open port 207 constructed to load and to hold a follicular unit 208, and the cannula 205 further having a tip 209 end constructed for insertion into an implantation incision at an implantation site; a flap 211 for at least partially closing the open port 207; a movable lever 213 hinged at one end to the cylindrical handle and connected at another end to the flap, the movable lever 213 being movable between a first position where the flap 211 closes the open port (as shown in FIGS. 2B and 2C) and a second position where the flap 211 is away from the open port and the port remains open (as shown in FIG. 2A); and a plunger 215 extending through the cannula 205 and constructed to displace a loaded follicular unit out from the cannula (as shown in FIG. 2C) into the implantation incision in a case where the movable lever is in the first position. In such an embodiment, the plunger is maintained in a relaxed or inactive conformation by a resilient device such as a spring (although other resilient devices can be envisioned). Compression of the spring results in actuation of the plunger. In the embodiment depicted, the tip 209 has a beveled edge sharp enough to penetrate tissue at an implantation site and create an incision site for the implantation of the follicular unit. However, in other embodiments the tip is non-incising. In alternative embodiments, the flap 211 has a beveled edge sharp enough to penetrate tissue at an implantation site and create an incision site for the implantation of the follicular unit.

Figure 3A:
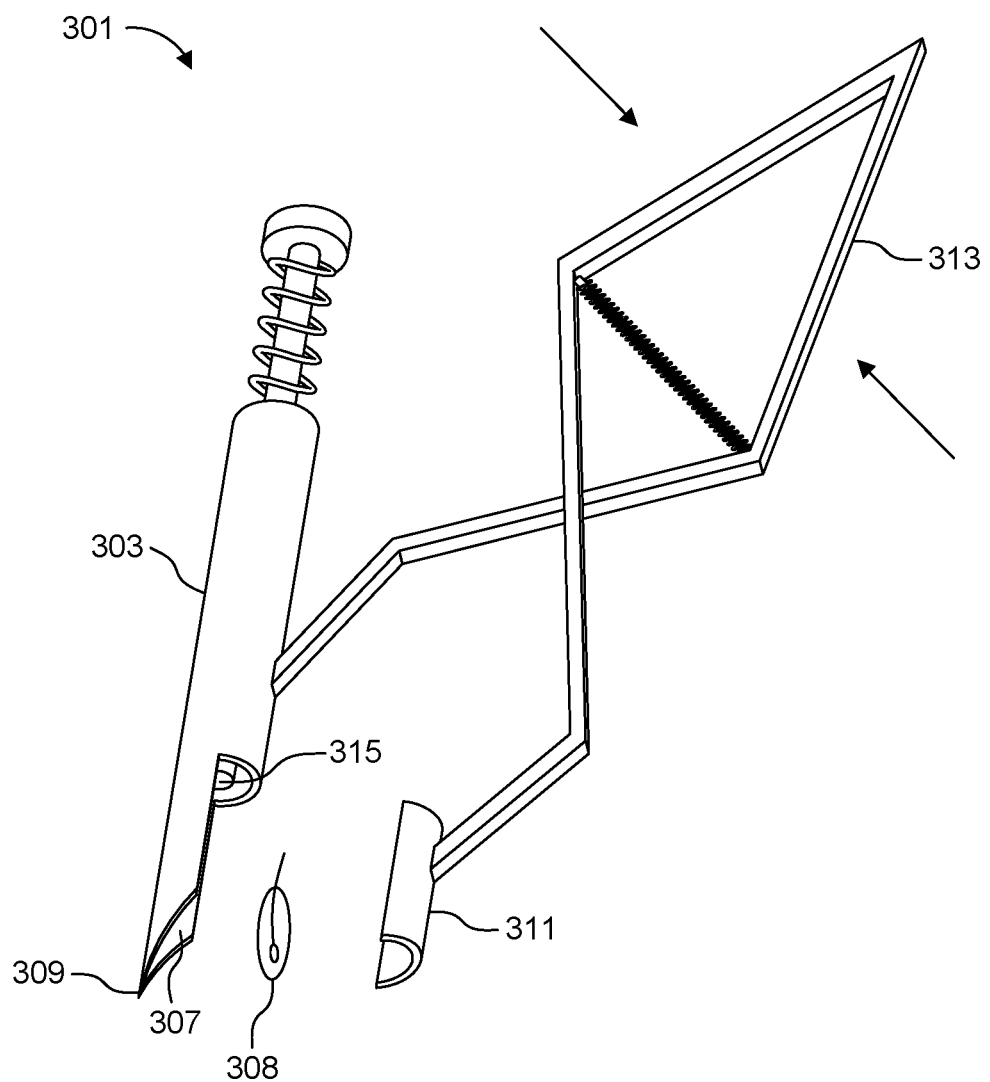
FIGS. 3A and 3B are illustrations depicting a surgical instrument for implantation of a follicular unit according to an embodiment of the disclosure.
Figure 3B:
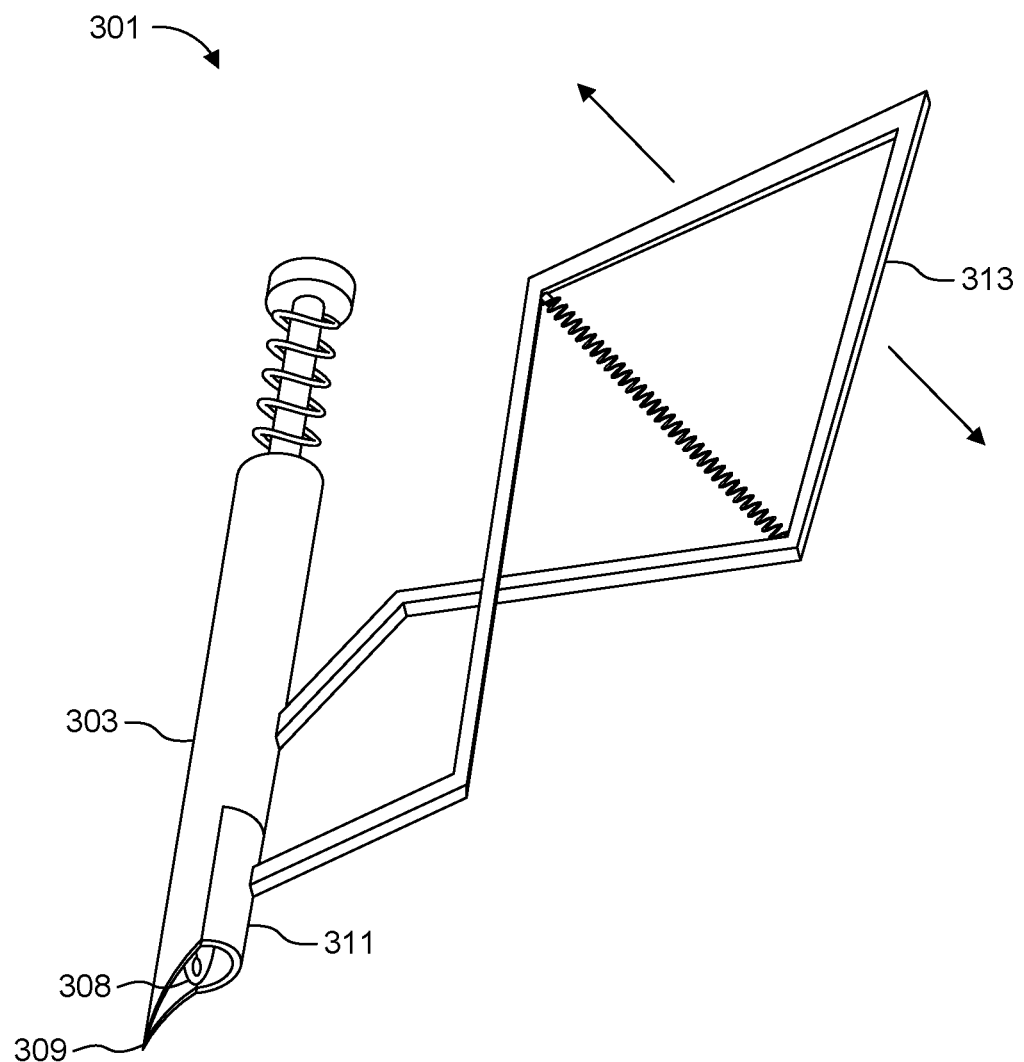

FIGS. 3A and 3B are illustrations of a surgical instrument 301 for implantation of a follicular unit according to an embodiment of the disclosure. The surgical instrument of FIGS. 3A and 3B includes: a generally cylindrical handle 303; a cannula 305 disposed at one end of the cylindrical handle 303, the cannula 305 having an open port 307 constructed to load and to hold a follicular unit 308, and the cannula 305 further having a tip 309 end constructed for insertion into an implantation incision at an implantation site; a flap 311 for at least partially closing the open port 307; a pair of forceps connected at one end thereof relative to the cylindrical handle and connected at another end thereof to the flap, the pair of forceps 313 being movable between a first position where the flap 311 closes the open port (as shown in FIG. 3B) and a second position where the flap 311 is away from the open port and the port remains open (as shown in FIG. 3A); and a plunger 315 extending through the cannula 305 and constructed to displace a loaded follicular unit out from the cannula into the implantation incision in a case where the pair of forceps is in the first position. In such an embodiment, a resilient device such as a spring maintains the forceps in the second position when at rest as indicated by the arrows (as shown in FIG. 3B). Compression of the resilient device, as shown by the arrows in FIG. 3A, results in the forceps adopting the second position where the flap 311 moves away from the open port and the port remains open. Also, in such an embodiment, the plunger is maintained in a relaxed or inactive conformation by a resilient device such as a spring (although other resilient devices can be envisioned). Compression of the spring results in actuation of the plunger. In the embodiment depicted, the tip 309 has a beveled edge sharp enough to penetrate tissue at an implantation site and create an incision site for the implantation of the follicular unit. However, in other embodiments the tip is non-incising. In alternative embodiments, the flap 311 has a beveled edge sharp enough to penetrate tissue at an implantation site and create an incision site for the implantation of the follicular unit.

Figure 4A:
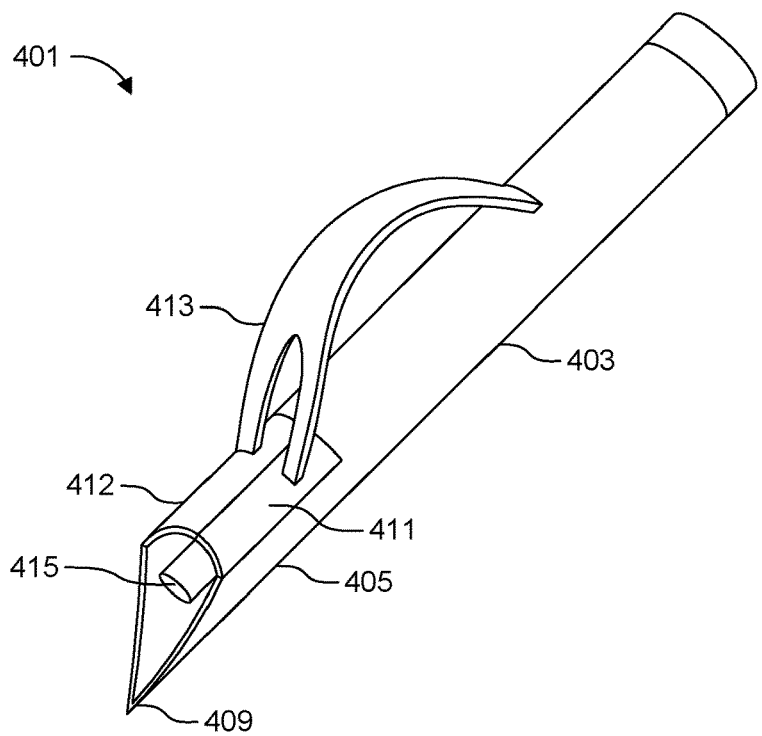
FIGS. 4A and 4B are illustrations depicting a surgical instrument for implantation of a follicular unit according to an embodiment of the disclosure.
Figure 4B:
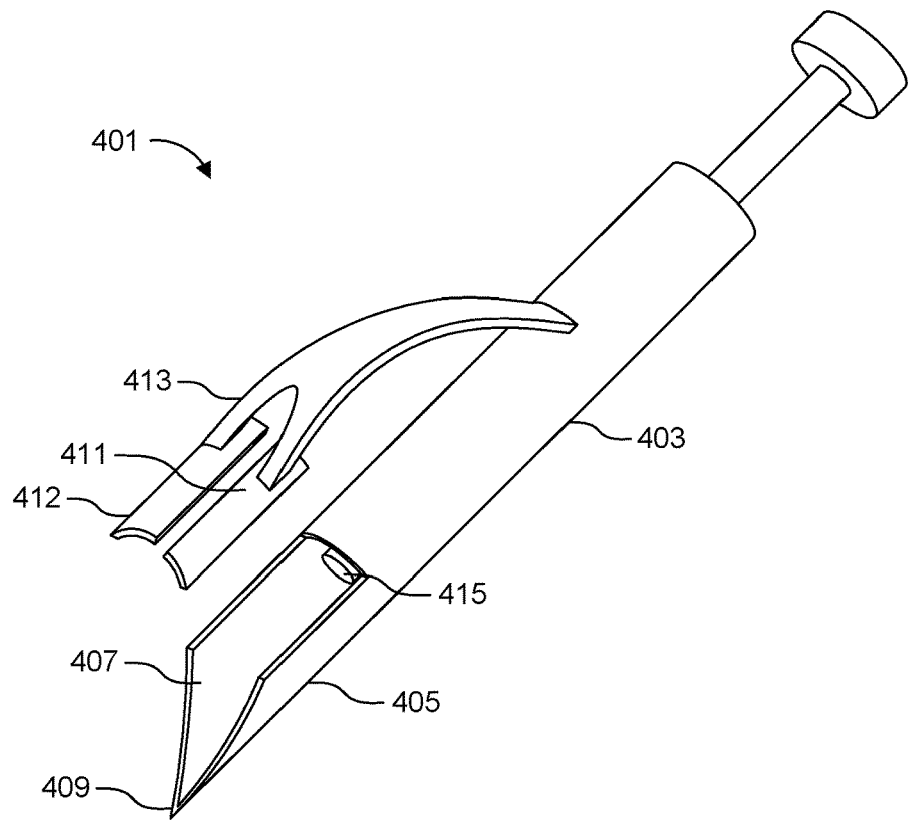

FIGS. 4A and 4B are illustrations of a surgical instrument 401 for implantation of a follicular unit according to an embodiment of the disclosure. The surgical instrument of FIGS. 4A and 4B includes: a generally cylindrical handle 403; a cannula 405 disposed at one end of the cylindrical handle 403, the cannula 405 having an open port 407 constructed to load and to hold a follicular unit, and the cannula 405 further having a tip 409 end constructed for insertion into an implantation incision at an implantation site; a multiple flaps 411, 412 for at least partially closing the open port 407; a movable lever 413 hinged at one end to the cylindrical handle and connected to each of the multiple flaps, the movable lever 413 being movable between a first position where the multiple flaps 411, 412 close the open port (as shown in FIG. 4A) and a second position where the multiple flaps 411, 412 are away from the open port and the port remains open (as shown in FIG. 4B); and a plunger 415 extending through the cannula 405 and constructed to displace a loaded follicular unit out from the cannula into the implantation incision in a case where the movable lever is in the first position. In the embodiment depicted, the tip 409 has a beveled edge sharp enough to penetrate tissue at an implantation site and create an incision site for the implantation of the follicular unit. However, in other embodiments the tip is non-incising. In alternative embodiments, at least one of the flaps 411, 412 has a beveled edge sharp enough to penetrate tissue at an implantation site and create an incision site for the implantation of the follicular unit.

Figure 5A:
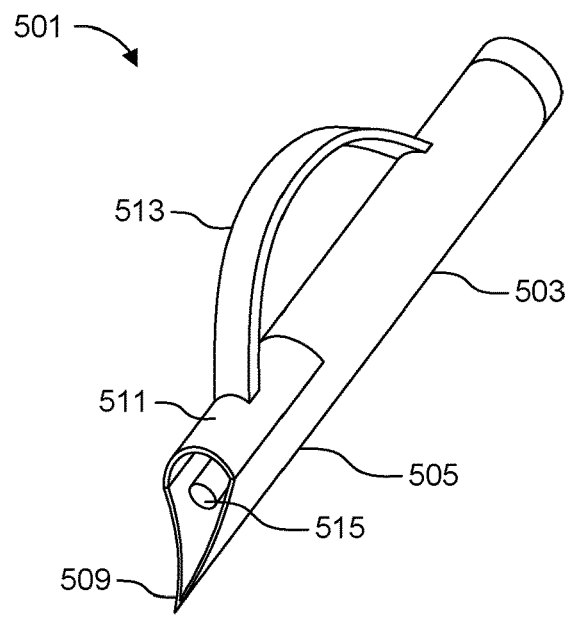
FIGS. 5A and 5B are illustrations depicting a surgical instrument for implantation of a follicular unit according to an embodiment of the disclosure.
Figure 5B:
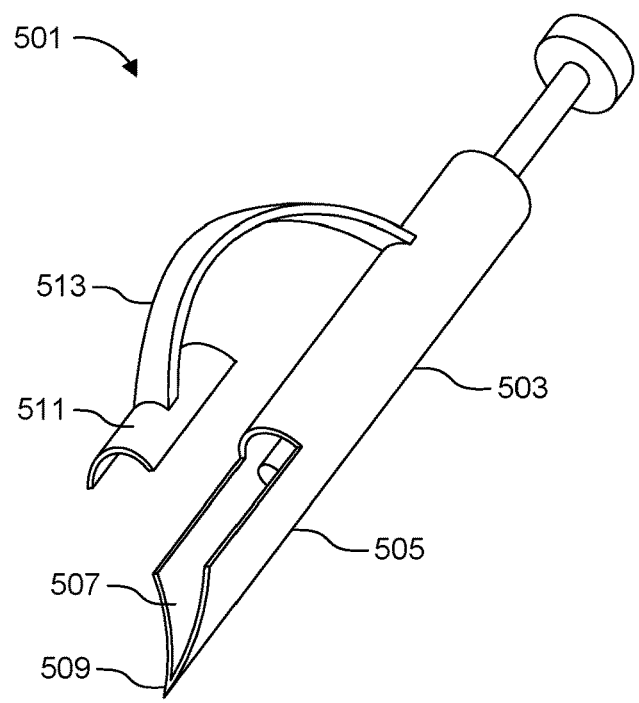

FIGS. 5A and 5B are illustrations of a surgical instrument 501 for implantation of a follicular unit according to an embodiment of the disclosure. The surgical instrument of FIGS. 5A and 5B includes: a generally cylindrical handle 503; a cannula 505 disposed at one end of the cylindrical handle 503, the cannula 505 having an open port 507 constructed to load and to hold a follicular unit, where the open port 507 extends longitudinally along the cannula 505 and radially across about one third of the cannula 505, and the cannula 505 further having a tip 509 end constructed for insertion into an implantation incision at an implantation site; a flap 511 for at least partially closing the open port 507; a movable lever 513 hinged at one end thereof relative to the cylindrical handle and connected at another end thereof to the flap, the movable lever 513 being movable between a first position where the flap 511 closes the open port (as shown in FIG. 5A) and a second position where the flap 511 is away from the open port and the port remains open (as shown in FIG. 5B); and a plunger 515 extending through the cannula 505 and constructed to displace a loaded follicular unit out from the cannula into the implantation incision in a case where the movable lever is in the first position. In the embodiment depicted, the tip 509 has a beveled edge sharp enough to penetrate tissue at an implantation site and create an incision site for the implantation of the follicular unit. However, in other embodiments the tip is non-incising. In alternative embodiments, the flap 511 has a beveled edge sharp enough to penetrate tissue at an implantation site and create an incision site for the implantation of the follicular unit.

Figure 6A:
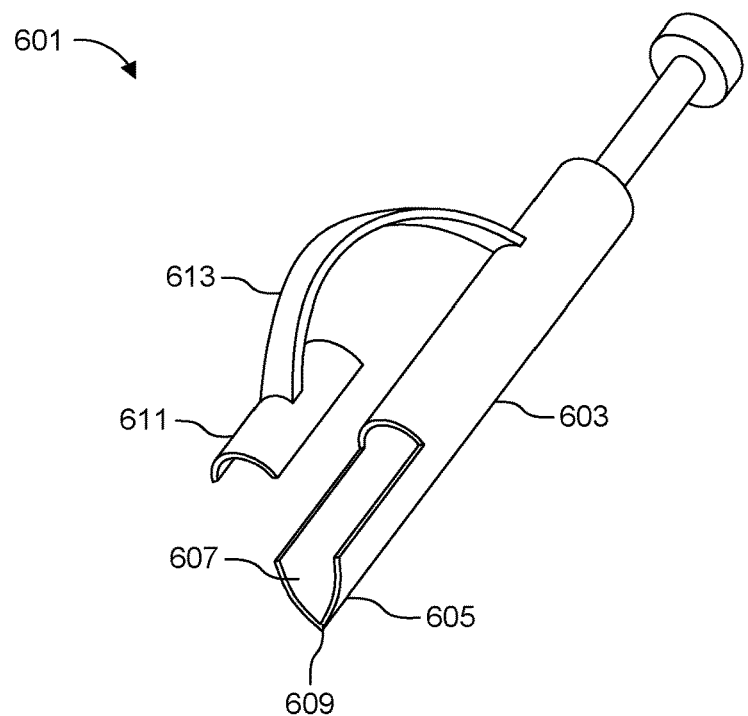
FIGS. 6A and 6B are illustrations depicting a surgical instrument for implantation of a follicular unit according to an embodiment of the disclosure.
Figure 6B:
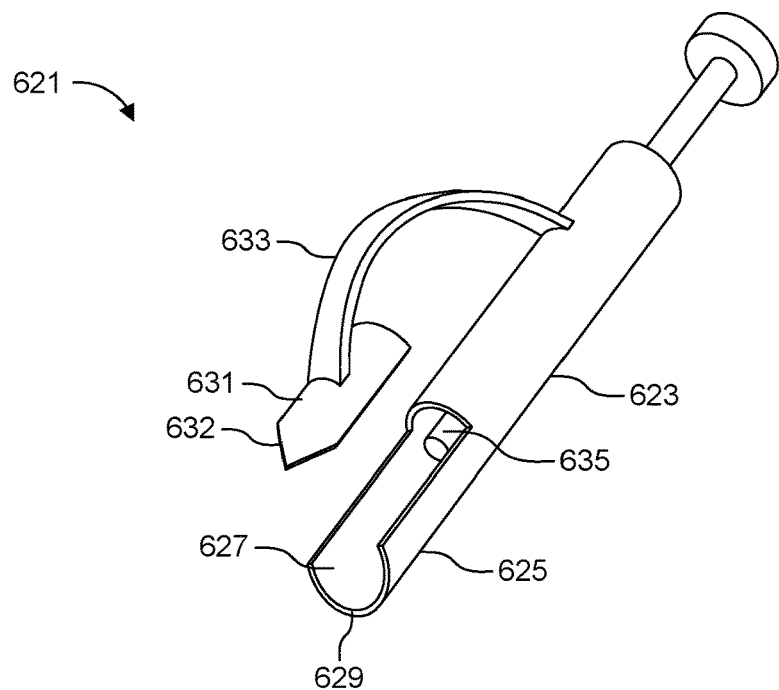

FIGS. 6A and 6B are illustrations of surgical instruments for implantation of a follicular unit according to embodiments of the disclosure.

The surgical instrument 601 of FIG. 6A includes: a generally cylindrical handle 603; a cannula 605 disposed at one end of the cylindrical handle 603, the cannula 605 having an open port 607 constructed to load and to hold a follicular unit, and the cannula 605 further having a non-incising pointed tip 609 end constructed for insertion into an implantation incision at an implantation site; a flap 611 for at least partially closing the open port 607; a movable lever 613 hinged at one end thereof relative to the cylindrical handle and connected at another end thereof to the flap, the movable lever 613 being movable between a first position where the flap 611 closes the open port and a second position where the flap 611 is away from the open port and the port remains open; and a plunger (not shown) extending through the cannula 605 and constructed to displace a loaded follicular unit out from the cannula into the implantation incision in a case where the movable lever is in the first position. In the embodiment depicted, the tip 609 is non-incising. In other embodiments, the tip 609 has a beveled edge sharp enough to penetrate tissue at an implantation site and create an incision site for the implantation of the follicular unit.

The surgical instrument 621 of FIG. 6B includes: a generally cylindrical handle 623; a cannula 625 disposed at one end of the cylindrical handle 623, the cannula 625 having an open port 627 constructed to load and to hold a follicular unit, and the cannula 625 further having a tip 629 end constructed for insertion into an implantation incision at an implantation site; a flap 631 having a non-incising pointed tip 632 for at least partially closing the open port 627; a movable lever 633 hinged at one end thereof relative to the cylindrical handle and connected at another end thereof to the flap, the movable lever 633 being movable between a first position where the flap 631 closes the open port and a second position where the flap 631 is away from the open port and the port remains open; and a plunger 635 extending through the cannula 625 and constructed to displace a loaded follicular unit out from the cannula into the implantation incision in a case where the movable lever is in the first position. In the embodiment depicted, the flap 631 has a non-incising pointed tip 632. In other embodiments, the flap 631 has a beveled edge sharp enough to penetrate tissue at an implantation site and create an incision site for the implantation of the follicular unit.

Figure 8A:
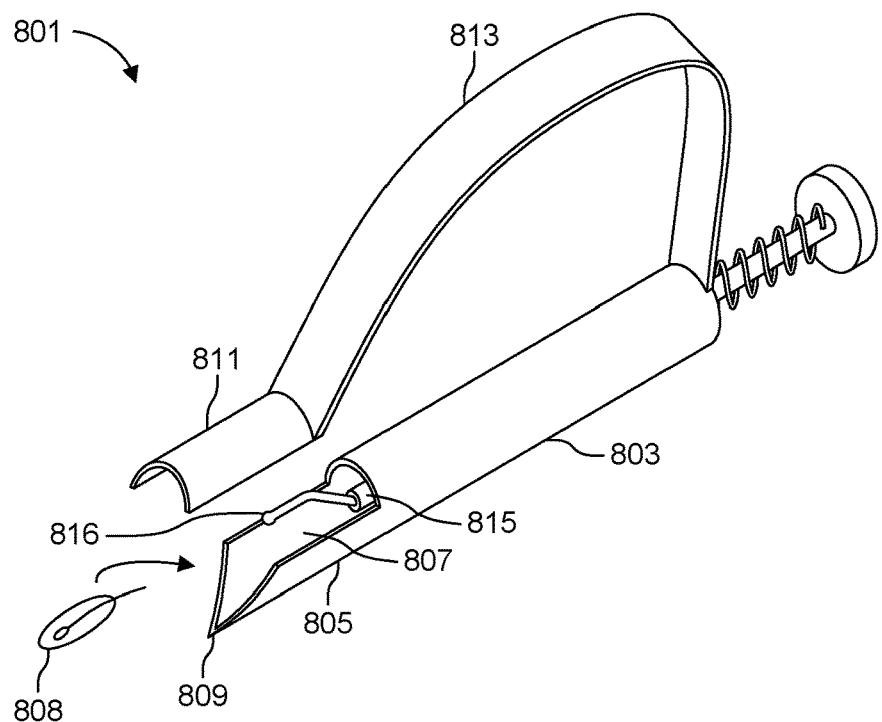
FIG. 8A is an illustration depicting a surgical instrument for implantation of a follicular unit according to an embodiment of the disclosure.
Figure 8B:
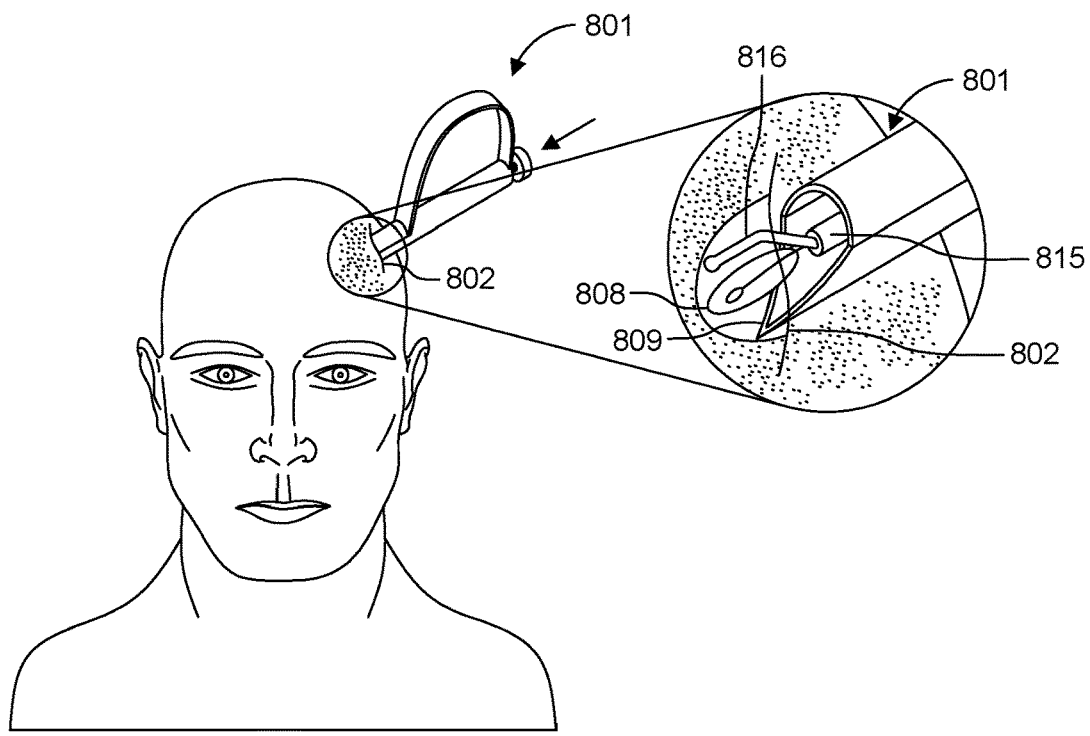
FIG. 8B is an illustration depicting a method for surgical implantation of a follicular unit into an implantation incision at an implantation site using the surgical instrument of FIG. 8A according to an embodiment of the disclosure.

FIG. 8A is an illustration of a surgical instrument 801 for implantation of a follicular unit according to an embodiment of the disclosure. The surgical instrument of FIG. 8A includes: a generally cylindrical handle 803; a cannula 805 disposed at one end of the cylindrical handle 803, the cannula 805 having an open port 807 constructed to load and to hold a follicular unit 808, and the cannula 805 further having a tip 809 end constructed for insertion into an implantation incision at an implantation site; a flap 811 for at least partially closing the open port 807; a movable lever 813 hinged at one end thereof relative to the cylindrical handle and connected at another end thereof to the flap, the movable lever 813 being movable between a first position where the flap 811 closes the open port and a second position where the flap 811 is away from the open port and the port remains open; and a plunger 815 extending through the cannula 805 and constructed to displace a loaded follicular unit out from the cannula into the implantation incision in a case where the movable lever is in the first position. The plunger 815 also includes a guiding member 816 to help guide transplantation of the follicular unit 803 during surgical implantation. As shown in FIG. 8B, during a surgical implantation procedure, surgical instrument 801 is brought into contact with an incision site 802. Operation of the plunger 815 simultaneously results in actuation of the guiding member 816 during implantation of the follicular unit 808 into the incision site 802 to ensure proper implantation of the follicular unit 808. In the embodiment depicted, the tip 809 has a beveled edge sharp enough to penetrate tissue at an implantation site and create an incision site for the implantation of the follicular unit. However, in other embodiments the tip is non-incising. In alternative embodiments, the flap 811 has a beveled edge sharp enough to penetrate tissue at an implantation site and create an incision site for the implantation of the follicular unit.

Figure 9:
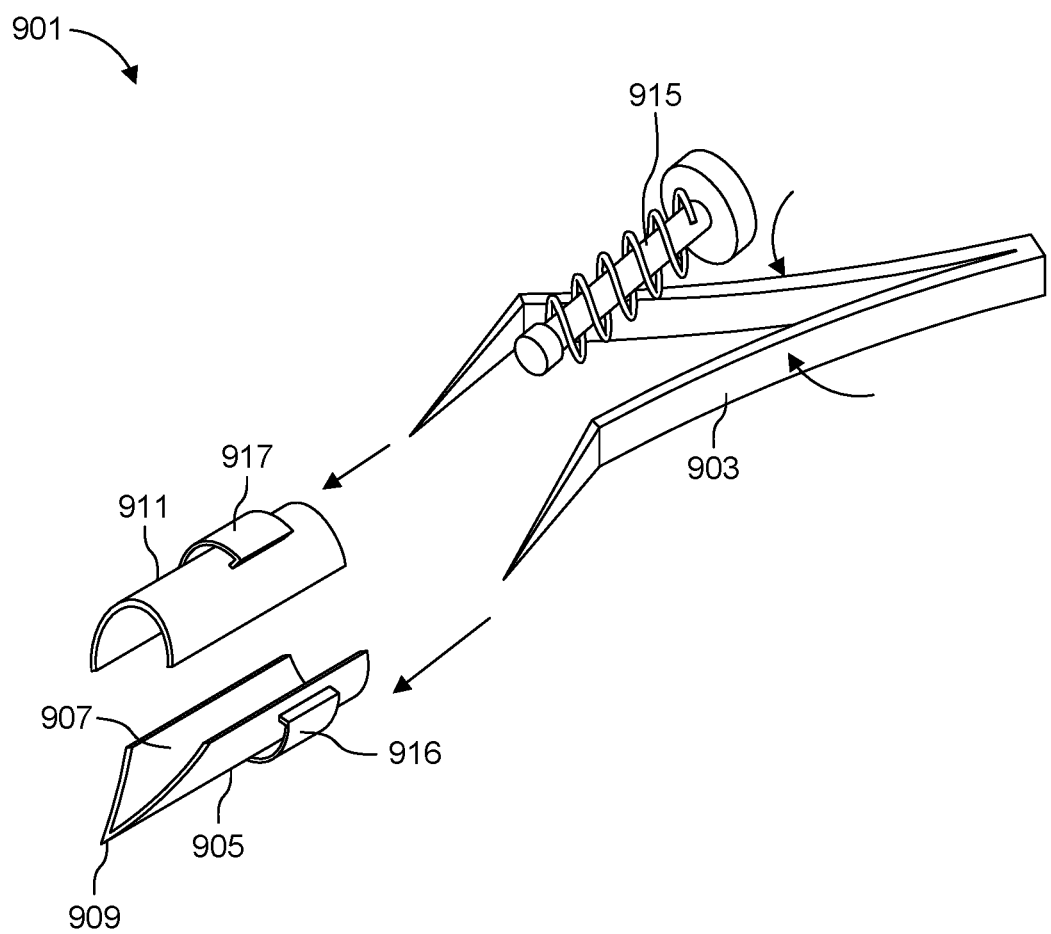
FIG. 9 is an illustration depicting a surgical instrument for implantation of a follicular unit according to an embodiment of the disclosure.

FIG. 9 is an illustration of a surgical instrument 901 for implantation of a follicular unit according to an embodiment of the disclosure. The surgical instrument of FIG. 9 includes: a pair of forceps 903; a cannula 905, the cannula 905 having an open port 907 constructed to load and to hold a follicular unit, and the cannula 905 further having a tip 909 end constructed for insertion into an implantation incision at an implantation site; a flap 911 for at least partially closing the open port 907; and a plunger 915 operably attached to the forceps. The cannula 905 and the flap 911 each further include a pocket structure 916, 917, respectively, configured to accept a tip end of the forceps during use (as indicated by the arrows). The forceps 903 are hinged at one end thereof relative to the cannula 905 and flap 911. When in use, the forceps 903 are movable between a first position where the flap 911 closes the open port and a second position where the flap 911 is away from the open port and the port remains open. The plunger 915 is configured to extend through the cannula 905 and to displace a loaded follicular unit out from the cannula into the implantation incision in a case where the forceps are in the first position. In such an embodiment, the forceps 903 are made of a durable material suitable for reuse (e.g. stainless steel), while the cannula 905 and flap 911 are designed for disposal following a procedure and are accordingly made of a durable and/or economic material (e.g. a plastic); additional suitable materials are readily apparent to one of ordinary skill in the art. In such an embodiment, the forceps 903 are serializable. Also, the cannula 905 and flap 911 can be prepackaged in a kit, and the kit can include multiple pairs or sets of complimentary cannulas and flaps. Alternative structures for attaching the cannula 905 and flap 911 to the forceps 903 can be readily envisioned by one of ordinary skill in the art. Such additional structures can be configured to provide a more secure fit between the cannula 905, flap 911 and forceps 903, for example. In the embodiment depicted, the tip 909 has a beveled edge sharp enough to penetrate tissue at an implantation site and create an incision site for the implantation of the follicular unit. However, in other embodiments the tip is non-incising. In alternative embodiments, the flap 911 has a beveled edge sharp enough to penetrate tissue at an implantation site and create an incision site for the implantation of the follicular unit.

Method

An embodiment of the instant disclosure herein relates to a method for surgical implantation of a follicular unit into an implantation incision at an implantation site, including the steps of: loading a follicular unit into the open port of the surgical instrument described above while the movable lever is in the second position where the flap is away from the open port; moving the movable lever to the first position where the flap at least partially closes the open port; inserting the tip end of the cannula into the implantation incision down to an implantation depth; and operating the plunger while the tip end of the cannula is inserted into the implantation incision and the movable lever is in the first position where the flap closes the open port, so as to displace the loaded follicular unit into the implantation site that is either previously made or made by the instrument at the time of insertion, while simultaneously withdrawing the tip end of the cannula from the implantation site.

An embodiment of the instant disclosure herein relates to the method for surgical implantation of a follicular unit into an implantation incision at an implantation site described above, where the tip end of the cannula has sharp edge configured to penetrate a tissue at the implantation site, where inserting the tip end of the cannula comprises creation of the implantation incision, and where at least the steps of loading a follicular unit into the open port of the surgical device, and inserting the tip end of the cannula into the implantation incision site are completed by a single user.

An embodiment of the instant disclosure herein relates to the method for surgical implantation of a follicular unit into an implantation incision at an implantation site described above, where the step of moving the movable lever to the first position where the flap closes the open port comprises moving the movable lever against a bias which biases the movable lever to the second position where the flap is away from the open port.

An embodiment of the instant disclosure herein relates to the method for surgical implantation of a follicular unit into an implantation incision at an implantation site described above, where before the step of loading a follicular unit into the open port of the surgical instrument, the method further comprises moving the movable lever to the second position where the flap is away from the open port against a bias which biases the movable lever to the first position where the flap closes the open port.

Figure 7A:
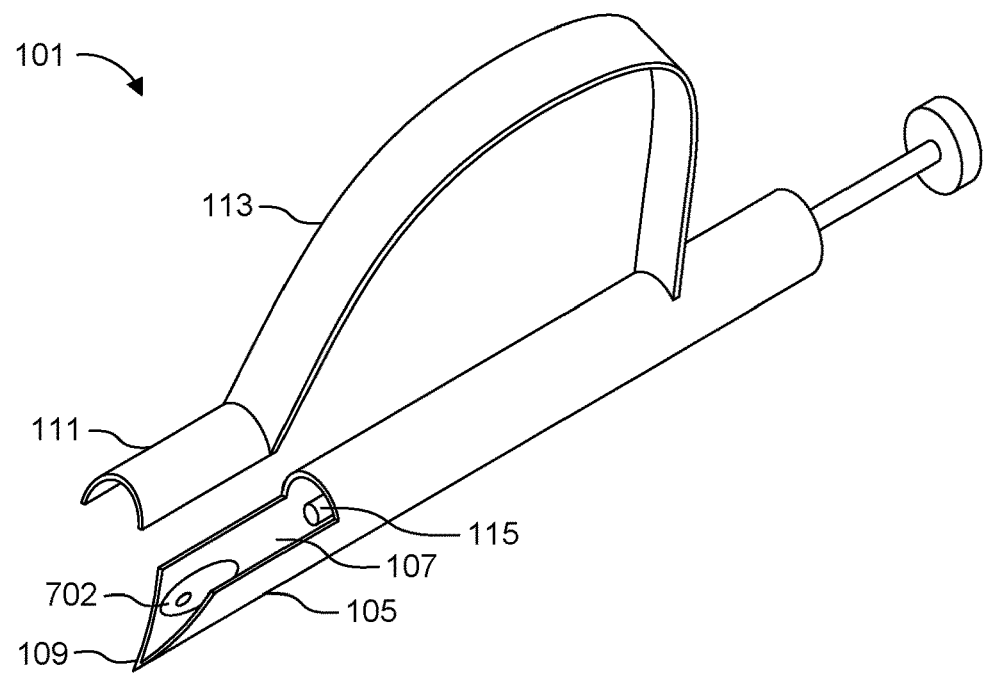
FIGS. 7A-7D are illustrations depicting a method for surgical implantation of a follicular unit into an implantation incision at an implantation site according to an embodiment of the disclosure.
Figure 7B:
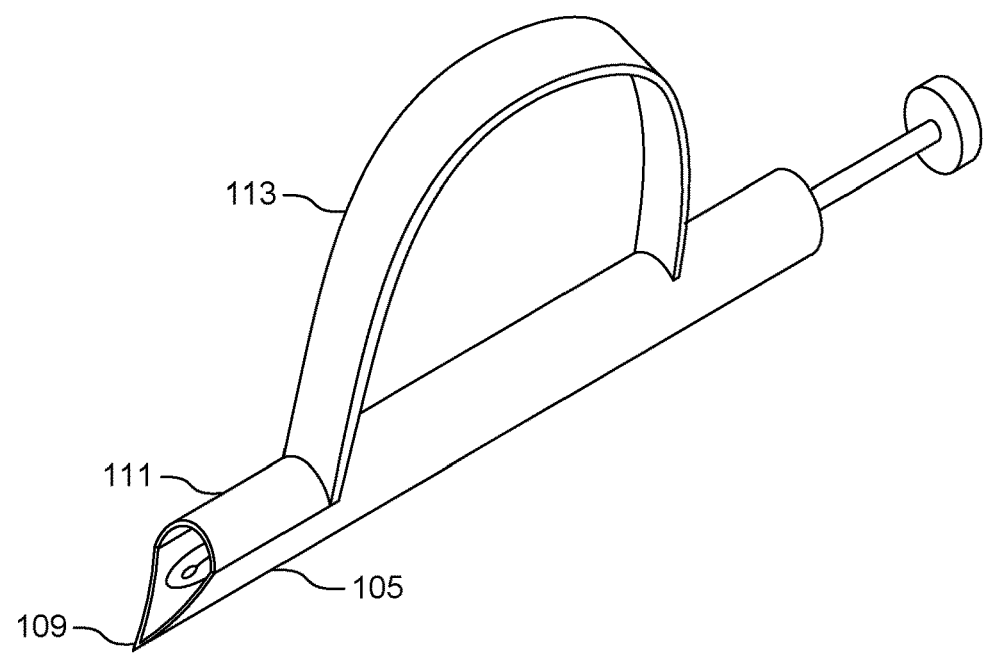
Figure 7C:
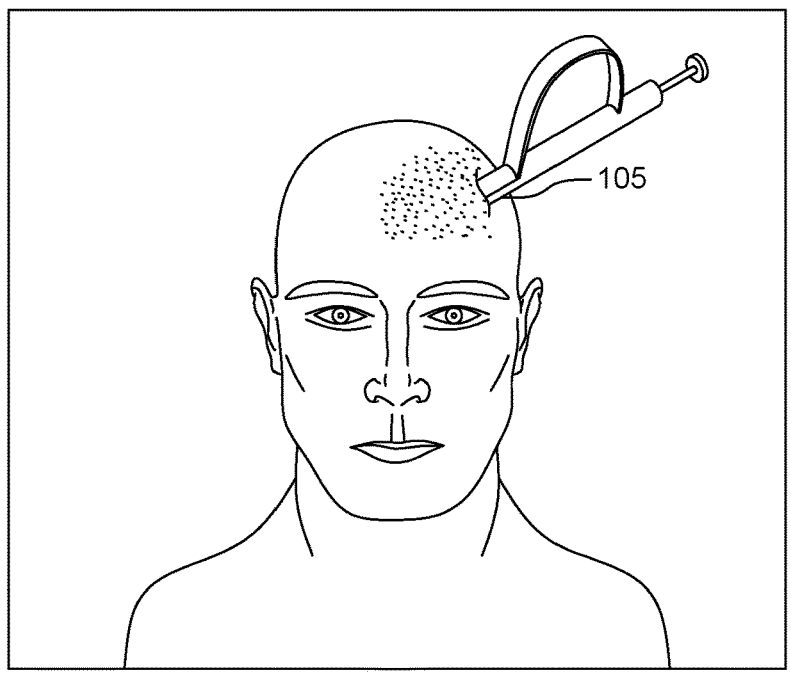
Figure 7D:
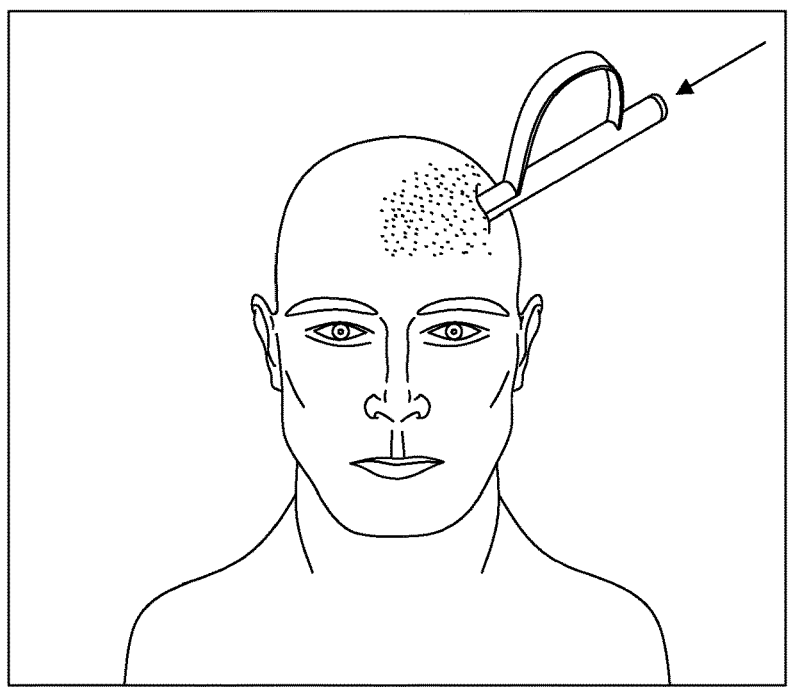

FIGS. 7A-7D show a method for surgical implantation of a follicular unit into an implantation incision at an implantation site according to an embodiment of the disclosure. As shown in FIG. 7A, the method includes the step of loading a follicular unit 702 into the open port 107 of the surgical instrument 101 of FIGS. 1A and 1B while the movable lever 113 of the surgical instrument is in the second position where the flap 111 is away from the open port 107. As shown in FIG. 7B, the method includes the step of moving the movable lever 113 to the first position where the flap 111 at least partially closes the open port. As shown in FIG. 7C, the method includes the step of inserting the tip end 109 of the cannula 105 into the implantation incision down to an implantation depth. As shown in FIG. 7D, the method includes the step of operating the plunger 115 (demonstrated by the arrow) while the tip 109 end of the cannula is inserted into the implantation incision and the movable lever is in the first position where the flap closes the open port, so as to displace the loaded follicular unit into the implantation site, while simultaneously withdrawing the tip end of the cannula from the implantation site. In the embodiment depicted, the tip 109 has a beveled edge sharp enough to penetrate tissue at an implantation site and create an incision site for the implantation of the follicular unit. However, in other embodiments the tip is non-incising. In alternative embodiments, the flap 111 has a beveled edge sharp enough to penetrate tissue at an implantation site and create an incision site for the implantation of the follicular unit.

Embodiments of the device described throughout can accommodate grafts of varying sizes. A harvested hair follicle is loaded into the cannula and is oriented such that the bulbar end of the follicular unit points toward the tip end of the cannula. Once the harvest hair follicle is loaded into the cannula, the open port of the cannula is closed and cannula is then gently inserted into the incision site without actuating the plunger. When the cannula is positioned properly inside the incision site, the plunger is actuated, directing the graft swiftly inside the incision site.

The embodiments illustrated and discussed in this specification are intended only to teach those skilled in the art how to make and use the disclosure herein. In describing embodiments of the disclosure herein, specific terminology is employed for the sake of clarity. However, the disclosure herein is not intended to be limited to the specific terminology so selected. The above-described embodiments of the disclosure herein may be modified or varied, without departing from the disclosure herein, as appreciated by those skilled in the art in light of the above teachings. It is therefore to be understood that, within the scope of the claims and their equivalents, the disclosure herein may be practiced otherwise than as specifically described.

The invention claimed is:

1. A surgical instrument for implantation of a follicular unit, comprising:
   a generally cylindrical handle;
   a cannula disposed at one end of the cylindrical handle, the cannula having an open port constructed to load and to hold a follicular unit, and the cannula further having a tip end constructed for insertion into an implantation incision at an implantation site;
   a flap for at least partially closing the open port;
   a movable lever hinged at one end thereof relative to the cylindrical handle and connected at another end thereof to the flap, the movable lever being movable between a first position where the flap closes the open port and a second position where the flap is completely away from the open port and the port remains open to facilitate loading of the follicular unit into the cannula through the open port; and
   a plunger extending through the cannula and constructed to displace a loaded follicular unit out from the cannula into the implantation incision in a case where the movable lever is in the first position, wherein at least one or both of the tip end of the cannula and the flap include a forwardly extending tip constructed for insertion to an implantation depth into the implantation incision.

2. The surgical instrument of claim 1, wherein the forwardly extending tip has a sharp edge configured to penetrate a tissue at the implantation site and to create the implantation incision at the implantation site.

3. The surgical instrument according to claim 1, wherein the open port extends longitudinally along the cannula.

4. The surgical instrument according to claim 1, wherein the open port extends longitudinally along the cannula and is open completely to the tip end of the cannula.

5. The surgical instrument according to claim 1, wherein the open port extends longitudinally along the cannula and is not open completely to the tip end of the cannula.

6. The surgical instrument according to claim 1, wherein the open port extends longitudinally along the cannula and radially across about half of the cannula.

7. The surgical instrument according to claim 1, wherein the open port extends longitudinally along the cannula and radially across about one third of the cannula.

8. The surgical instrument according to claim 1, wherein the forwardly extending tip of the cannula includes a non-incising pointed tip.

9. The surgical instrument according to claim 1, wherein the forwardly extending tip of the flap includes a non-incising pointed tip.

10. The surgical instrument according to claim 1, wherein the movable lever is biased in a direction towards the first position where the flap closes the open port, and movement of the movable lever against the bias causes movement of the movable lever towards the second position where the flap is away from the open port.

11. The surgical instrument according to claim 1, wherein the movable lever is biased in a direction towards the second position where the flap is away from the open port, and movement of the movable lever against the bias causes movement of the movable lever in toward the first position where the flap closes the open port.

12. The surgical instrument according to claim 1, wherein multiple flaps are actuated by the movable lever and cooperate for at least partial closing of the open port.

13. The surgical instrument according to claim 1, wherein the flap completely closes the open port.

14. The surgical instrument according to claim 1, wherein the forwardly extending tip of the cannula includes a sharp edge for penetration of tissue at the implantation site and for creation of the implantation incision at the implantation site.

15. The surgical instrument according to claim 1, wherein the forwardly extending tip of the flap includes a sharp edge for penetration of tissue at the implantation site and for creation of the implantation incision at the implantation site.

16. A method for surgical implantation of a follicular unit into an implantation incision at an implantation site, comprising:

loading a follicular unit into the open port of the surgical instrument as claimed in claim 1 while the movable lever is in the second position where the flap is away from the open port;

moving the movable lever to the first position where the flap at least partially closes the open port;

inserting the tip end of the cannula into the implantation incision down to an implantation depth; and operating the plunger while the tip end of the cannula is inserted into the implantation incision and the movable lever is in the first position where the flap closes the open port, so as to displace the loaded follicular unit into the implantation site, while simultaneously withdrawing the tip end of the cannula from the implantation site.

17. The method according to claim 16, wherein the tip end of the cannula has sharp edge configured to penetrate a tissue at the implantation site, wherein inserting the tip end of the cannula comprises creation of the implantation incision, and wherein at least the steps of loading a follicular unit into the open port of the surgical device, and inserting the tip end of the cannula into the implantation incision site are completed by a single user.

18. The method according to claim 16, wherein the step of moving the movable lever to the first position where the flap closes the open port comprises moving the movable lever against a bias which biases the movable lever to the second position where the flap is away from the open port.

19. The method according to claim 16, wherein before the step of loading a follicular unit into the open port of the surgical instrument, the method further comprises moving the movable lever to the second position where the flap is away from the open port against a bias which biases the movable lever to the first position where the flap closes the open port.

* * * * *